US006820485B2

(12) United States Patent
Grimshaw

(10) Patent No.: US 6,820,485 B2
(45) Date of Patent: Nov. 23, 2004

(54) METHOD AND APPARATUS FOR MEASURING FILM THICKNESS AND FILM THICKNESS GROWTH

(75) Inventor: Scott F. Grimshaw, Marcellus, NY (US)

(73) Assignee: Tangidyne Corporation, Marcellus, NY (US)

( * ) Notice: Subject to any disclaimer, the term of this patent is extended or adjusted under 35 U.S.C. 154(b) by 0 days.

(21) Appl. No.: 10/460,971

(22) Filed: Jun. 13, 2003

(65) Prior Publication Data

US 2004/0206182 A1 Oct. 21, 2004

Related U.S. Application Data

(60) Provisional application No. 60/464,237, filed on Apr. 21, 2003.

(51) Int. Cl.$^7$ .............................................. G01H 13/00
(52) U.S. Cl. ....................... 73/579; 73/24.06; 73/580; 427/9
(58) Field of Search .................. 73/579, 580, 24.06; 427/9; 310/361

(56) References Cited

U.S. PATENT DOCUMENTS

| 4,561,286 | A | * | 12/1985 | Sekler et al. .............. 73/24.06 |
|---|---|---|---|---|
| 6,247,354 | B1 | * | 6/2001 | Vig et al. ..................... 73/579 |
| 6,294,964 | B1 | * | 9/2001 | Satoh ..................... 331/116 R |
| 6,370,955 | B1 | * | 4/2002 | Tuller et al. .................. 73/579 |

OTHER PUBLICATIONS

Krempl, P., Schleinzer, G., Wallnöfer, W., "Gallium phosphate, GaPO$_4$; a new piezoelectric crystal material for high–temperature sensorics," Sensors and Actuators A61, 1997, pp. 361–363.

Mecea, V.M., Carrison, J.O., Heszlert, P., Bârtan, "Development and testing of a high temperature quartz crystal microbalance," Pergamon, 1995, Vacuum/vol. 46/No. 7, pp. 691–694.

* cited by examiner

*Primary Examiner*—John E. Chapman
(74) *Attorney, Agent, or Firm*—Burr & Brown

(57) ABSTRACT

A device for measuring thickness and/or rate of thickness increase of a film comprises at least one piezoelectric element, and first and second electrodes in contact with the piezoelectric element. A method of measuring thickness and/or rate of thickness increase of a film comprises applying a voltage across a piezoelectric element from a first electrode to a second electrode, thereby causing the piezoelectric element to vibrate, and measuring the rate of vibration of the piezoelectric element. Heat may be applied to the piezoelectric element. The piezoelectric element may be formed of quartz crystal, e.g., IT-cut.

15 Claims, 2 Drawing Sheets

METHOD AND APPARATUS FOR MEASURING FILM THICKNESS AND FILM THICKNESS GROWTH

This application claims benefit of 60/464,237 filed Apr. 21, 2003.

FIELD OF THE INVENTION

The present invention relates to an apparatus for measuring the thickness of a film, and/or for monitoring the rate of increase of the thickness of a film, and to a method for carrying out such measuring and/or monitoring. In one aspect, the present invention relates to a quartz crystal thickness monitor which provides coating rate and thickness data in real time by monitoring change in frequency of vibration of a test crystal coated simultaneously with one or more process substrates, e.g., in the fabrication of optical devices (such as lenses, filters, reflectors and beam splitters) by optical thin-film deposition systems in which evaporant is deposited from deposition sources.

BACKGROUND OF THE INVENTION

Since the early 1960's, quartz crystals have been used to monitor thin film coating processes used in the fabrication of optical devices such as lenses, filters, reflectors and beam splitters. Although initially employed as an aid to optical monitors to provide information on the rate at which the film is deposited, quartz crystal sensors became relied upon to indicate and control optical layer thickness in automated deposition systems.

Research in fields such as nanotechnology, biosensors, thin film displays, and high-speed optical communications have increased the complexity of thin film structures. While an antireflection coating consisting of a single layer of magnesium fluoride may have been sufficient 20 years ago, current designs may call for a 24-layer stack of alternating refractive index films. With high-speed optical communications, this stack increases ten-fold, leading to filters comprised of up to 256 layers.

The manufacturing of these geometries requires the control and accuracy provided by a quartz crystal. Unfortunately, the materials and deposition temperatures utilized in today's processing can adversely affect the operation of the crystal sensor.

Quartz crystal thickness monitors may be the most misunderstood components of optical thin film deposition systems. Quartz sensors provide process engineers with coating rate and thickness data in real time, with Angstrom resolution.

Quartz sensor instruments measure film thickness by monitoring a change in the frequency of vibration of a test crystal coated simultaneously with process substrates. Quartz is a piezoelectric material., i.e., if a bar of quartz is bent, it will develop a voltage on opposite faces. Conversely, if a voltage is applied, the bar will bend. By applying alternating voltage to such a bar, the bar will vibrate or oscillate in phase with the voltage.

At a specific frequency of oscillation, quartz will vibrate with minimal resistance, much like a tuning fork rings when struck. This natural resonance frequency is used as the basis for measuring film thickness. By adding coatings to the crystal surface, the resonance frequency decreases linearly. If the coatings are removed, the resonance frequency increases.

In a quartz crystal thickness monitor, the quartz crystal is coupled to an electrical circuit that causes the crystal to vibrate at its natural (or resonant) frequency, which for most commercial instruments is between 5 and 6 MHz. A microprocessor-based control unit monitors and displays this frequency, or derived quantities, continuously. As material coats the crystal during deposition, the resonant frequency decreases in a predictable fashion, proportional to the rate material arrives at the crystal, and the material density. The frequency change is calculated several times per second, converted in the microprocessor to Angstroms per second and displayed as deposition rate. The accumulated coating is displayed as total thickness.

The sensitivities of these sensors are remarkable. A uniform coating of as little as 10 Angstroms of aluminum will typically cause a frequency change of 20 Hz, easily measured by today's electronics. As the density of the film increases, the frequency shift per Angstrom increases.

The useful life of quartz is dependent on the thickness and type of coating monitored. If a low stress metal such as aluminum is deposited, layers as thick as 1,000,000 Angstroms have been measured. At the other extreme, highly stressful dielectric films can cause crystal malfunction at thicknesses as low as 2,000 Angstroms or less.

In the early days of crystal thickness monitors, metallic films of copper, silver and gold were the materials that were deposited the most commonly. These films produced coatings of low stress and were condensed on substrates held near room temperature. Under these conditions, very accurate determinations of film thickness and rate were achievable.

When the optics industry began to employ crystal monitors, attention shifted from opaque metals to transparent materials such magnesium fluoride, and silicon dioxide, since coatings had to transmit light. Unfortunately, these substances produced films with high intrinsic stresses and required high process or substrate temperatures. These were not welcome developments for crystal monitoring, as sensors which have employed quartz have been highly sensitive to stress and temperature changes.

This sensitivity can be traced to the piezoelectric properties of quartz. Further complicating matters is the fact that quartz crystal sensors which have been employed have exhibited frequency change when deformed by thin film stresses or mechanical forces, e.g., from a mounting holder. If process conditions heat or cool such sensors, a similar frequency shift occurs. Regardless of the origin, the frequency shift is indistinguishable from that caused by the addition of coating.

Frequency shifts can be positive or negative, and can be cumulative. They can also be random. Causes of resonant frequency changes include:

Vibrations introduced through the mounting hardware;

Variations in the voltage used to oscillate the crystal;

Changes in the film being monitored (acoustic impedance);

Adhesion failure of the monitored coating or quartz electrodes; and

Radio frequency interference in the monitoring circuit.

These effects introduce large errors in thickness and rate calculations. Temperature swings in quartz can result in thickness variations of 50 Angstroms or more (see FIG. 1, which is a plot of frequency shift vs. temperature for AT-cut quartz crystal). Adhesion failure results in 100-Angstrom rate spikes. Extraneous vibrations can produce changes in the thousand Angstrom range. For precision optical components, these errors result in major yield loss.

The harsh conditions present during optical film coating can have deleterious effects on the operating life of a crystal. High stress coatings can deform the crystal to the point that it ceases to oscillate, without warning. Splatters of material from the coating source can lead to similar failure. High-energy plasmas used for substrate cleaning can couple into the crystal electronics and cause severe electrical noise. High temperature depositions can overheat the crystal, driving it past its operating limit.

Early crystal failure can be a great inconvenience or an unmitigated disaster. In the case of 100+ layer thin film stacks, venting the chamber to replace crystals is not an option, due to the undesirable effects of atmospheric gases on film chemistry. For very thick films, used in laser power or infrared optics, short crystal life may prevent completion of the coating. For high-speed roll coating systems, abrupt crystal failure can cause great amounts of ruined substrates.

Attempts have been made to reduce crystal failure and increase accuracy, e.g., through the use of sensors made of AT-cut quartz and through the use of water-cooled holders and/or sensor heads in order to maintain the temperature of the sensor between 20 degrees C. and 45 degrees C., in which temperature range the AT-cut quartz is "substantially temperature insensitive," (see FIG. 1) in order to reduce thermally induced frequency shifts for low temperature processes.

That is, in the past, films have been deposited at elevated temperatures in order to attempt to alleviate stresses which result from the films being built up. However, because such elevated temperatures cause the sensor to move out of the "substantially temperature-insensitive region," and result in frequency shifts in the thickness measurements of such sensor systems (see FIG. 1), prior systems have used cooling systems to try to counteract the effects of such heating, and to try to maintain the temperature in the substantially "temperature-insensitive" region.

For example, conventional quartz crystal based thin film thickness sensor systems utilize a water cooled stainless steel holder which uses a thin (0.010" thick) quartz crystal disk to measure the thickness, in situ and real time, of a thin film deposition process. This technology, available since the early 1960's, is difficult to use when optical materials, such as magnesium fluoride, or silicon dioxide, are used in the coating process. These materials cause the crystal to act erratically and fail prematurely during the coating process, preventing the measurement and control function from taking place. It is thought that the intrinsic stresses that these materials have when deposited as thin films result in the quartz becoming strained microscopically. Typically, lenses to be coated are heated during coating to alleviate this stress.

The quartz sensor, placed near the structures (e.g., lenses) being deposited to monitor the process, has historically been water cooled at the same time, to minimize fluctuations in its reading due to temperature changes resulting from process heat (i.e., heat resulting from the process being used to deposit the coating). This cooling, unfortunately, compounds the stress problem on the crystal surface. Moreover, recent studies of standard sensor heads show that even with water-cooling, the crystal temperature can rise 20 to 30 degrees within a 10-minute process. For extended runs with high chamber temperatures, temperature increases can become considerably larger.

Others have attempted to generate temperature-frequency algorithms to try to cancel out the component of frequency change caused by temperature. Examples of such work include: (1) E. C. van Ballegooijen, "Simultaneous Measurement of Mass and Temperature using Quartz Crystal Microbalances" Chapter 5, Methods and Phenomena 7, C. Lu and A. W. Czandema, Editors, Applications of Piezoelectric Quartz Crystal Microbalances, Elsevier Publishing, New York, 1984, and (2) E. P. Eernisse, "Vacuum Applications of Quartz Resonators", J. Vac. Sci. Technol., Vol. 12, No. 1, January/February 1975, pp 564–568.

A paradigm shift is underway in quartz crystal process monitoring. In many applications, crystals become the keys to success. No matter how significant a breakthrough may be in optics, be it materials, geometry, process design or application, if a thin film coating of any sophistication is required, the weak link is how accurately that film can be measured. As technology closes in on manipulating Angstrom-level properties of matter, the need for reliable thin film metrology rises to a new level of importance.

Film stress, adhesion failure, and extreme temperature effects have not been adequately dealt with. The current demands of nanotechnology, thin film displays, and high speed optical communications bring about an increased need for a quartz crystal monitor which reduces these inaccuracies and which reduces the frequency of such malfunctioning.

BRIEF SUMMARY OF THE INVENTION

In accordance with a first aspect of the present invention, instead of trying to cool the piezoelectric element to counteract the effects of process heat being applied to the piezoelectric element, heat is directly applied to the piezoelectric element in order to heat the piezoelectric element to a temperature which is equal to or greater than the process conditions, such that stress is reduced, and even though the temperature is outside the "substantially temperature-insensitive range," because the temperature of the piezoelectric element is above the temperature of the processing, the temperature of the piezoelectric element can be maintained at a specific value, thereby eliminating any substantial frequency shift resulting from temperature variance.

According to this first aspect of the present invention, there is provided a device for measuring the thickness of a film and/or the rate of increase of the thickness of a film, the device comprising:

at least one piezoelectric element;

a first electrode, the first electrode being in contact with a first region of the piezoelectric element;

a second electrode, the second electrode being in contact with a second region of the piezoelectric element, the second region being spaced from the first region; and a heater which heats the piezoelectric element.

Preferably, the heater heats the piezoelectric element to a temperature of at least about 50 degrees C., more preferably at least about 100 degrees C. The heater preferably maintains the piezoelectric element at a substantially constant temperature.

In accordance with a second aspect of the present invention, instead of the use of a sensor made of AT-cut quartz, the sensor is constructed of a different cut of quartz, namely, IT-cut quartz.

It has been surprisingly found that IT-cut quartz crystal provides performance superior to the industry standard AT-cut when used as a quartz crystal microbalance (i.e., thin film thickness sensor). The primary advantage to the sensor according to this aspect of the invention is the lack of substantial response to radiation induced frequency changes caused by heat sources or hot deposition sources present in a high vacuum thin film deposition system. When an AT-cut crystal in a conventional device is illuminated by a radiant source (such as a quartz lamp used to heat the substrates being coated), the sudden rise in temperature produces a sharp jump in oscillating frequency. This jump can be confused with frequency changes caused by the addition of mass to the crystal from the deposition source. Hence, an error in the accuracy of the film thickness is inadvertently introduced.

A second benefit of the sensor made of IT-cut quartz crystal according to this aspect of the invention is its diminished stress-frequency response. As an AT-cut crystal in a conventional device is deformed by the accumulation of high stress coatings (e.g., dielectrics used in optical coating processes), a frequency shift is introduced that, as in the radiation example, is indistinguishable from the frequency shift caused by mass accumulation. The IT-cut does not exhibit these frequency shifts to the degree of the AT-cut. Further, the useable life of an IT-cut quartz crystal microbalance is significantly longer than an AT-cut since stress-induced frequency noise does not obscure the mass-frequency behavior as readily.

According to this second aspect of the present invention, there is provided a device for measuring the thickness of a film and/or the rate of increase of the thickness of a film, the device comprising:

at least one piezoelectric element, the piezoelectric element comprising IT-cut quartz crystal;

a first electrode, the first electrode being in contact with a first region of the piezoelectric element; and a second electrode, the second electrode being in contact with a second region of the piezoelectric element, the second region being spaced from the first region.

According to another aspect, the present invention is directed to a method of measuring the thickness of a film and/or the rate of increase of the thickness of a film, the method comprising:

applying a voltage across a piezoelectric element from a first electrode to a second electrode, thereby causing the piezoelectric element to vibrate, the first electrode being in contact with a first region of the piezoelectric element, the second electrode being in contact with a second region of the piezoelectric element;

applying heat to the piezoelectric element; and measuring the rate of vibration of the piezoelectric element.

According to another aspect, the present invention is directed to a method of measuring the thickness of a film and/or the rate of increase of the thickness of a film, the method comprising:

applying a voltage across a piezoelectric element comprising IT-cut quartz crystal from a first electrode to a second electrode, thereby causing the piezoelectric element to vibrate, the first electrode being in contact with a first region of the piezoelectric element, the second electrode being in contact with a second region of the piezoelectric element; and measuring the rate of vibration of the piezoelectric element.

The devices according to the present invention can be used to automatically control deposition sources, ensure repeatable and accurate thin film coatings, and control optical film properties dependent on deposition rate. The present invention provides improved accuracy.

The invention may be more fully understood with reference to the accompanying drawings and the following detailed description of the invention.

BRIEF DESCRIPTION OF THE DRAWING FIGURES

DETAILED DESCRIPTION OF THE INVENTION

Figure 1:
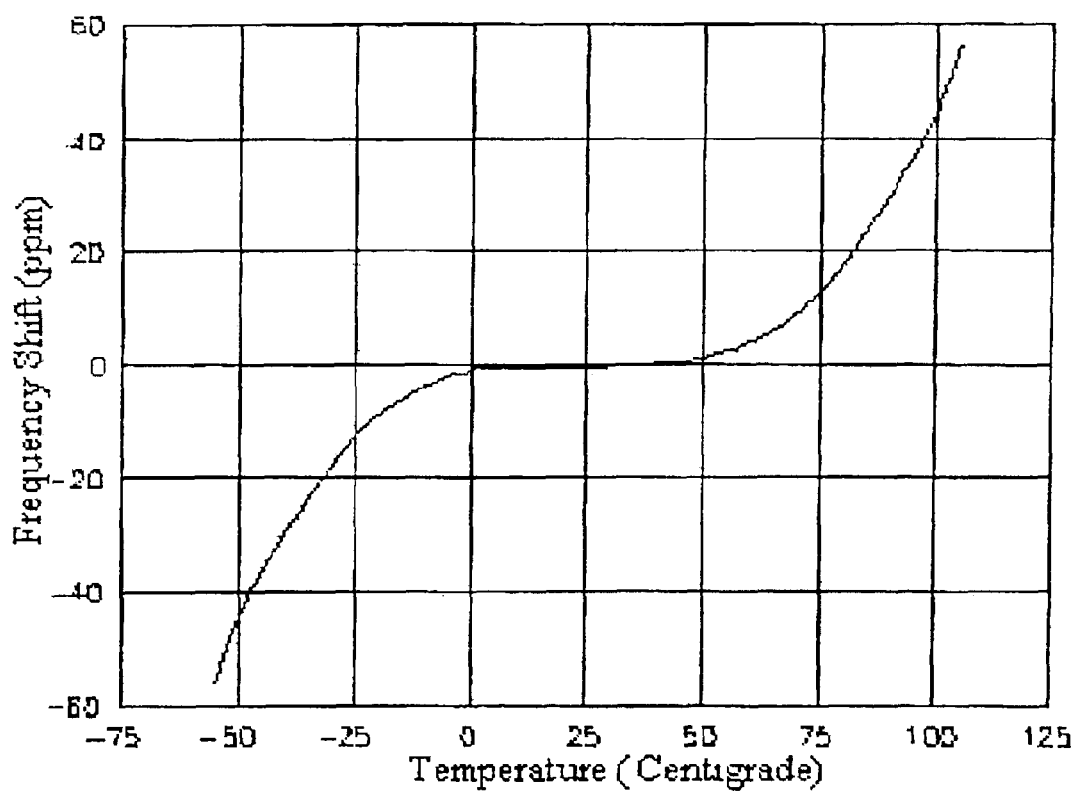
FIG. 1 is a plot of frequency shift vs. temperature for AT-cut quartz crystal

In an example of a system which employs a sensor according to the present invention, a piezoelectric element crystal sensor is contained in a housing, mounted in a line-of-sight position relative to a coating source (electron beam, thermal evaporation, sputtering, etc.). Substrates to be coated are positioned close to the crystal, ensuring that the amount of material (e.g., evaporant) depositing on the substrates and crystal are substantially identical. If this is not the case, a geometrical correction or "tooling factor," is applied.

As noted above, the device for measuring the thickness of a film and/or the rate of increase of the thickness of a film according to the present invention comprises at least one piezoelectric element, and first and second electrodes. In accordance with one aspect of the present invention, there is further provided a heater which heats the piezoelectric element.

The piezoelectric element can generally be made of any piezoelectric material, e.g., quartz, gallium phosphide, langasites or langatites. A preferred piezoelectric material is quartz crystal.

In cases where the piezoelectric material is quartz crystal, the crystal is preferably a singly rotated cut (e.g., an AT-cut crystal) or a doubly rotated cut (e.g., an IT-cut crystal or an SC-cut crystal), such crystal cuts being well known to those of skill in the art.

The AT-cut is a member of the family of singly rotated cuts; it is formed by aligning the plane of the saw blade with the X-Z crystal axes, and then rotating the blade about the X axis until reaching an angle (referred to as the angle θ) of about 35°, preferably about 35° 15', plus or minus about 20'. AT-cuts exhibit little frequency change with temperature change within a range of temperature (as noted above, from 20 degrees C. to 45 degrees C., the AT-cut quartz is "substantially temperature insensitive"). The angle of cut can be varied (e.g., by up to 20 minutes or more) to allow stable operation at somewhat higher or lower temperatures as well.

SC-cut and IT-cut crystals are doubly rotated cuts. Such cuts can be formed by aligning the plane of the saw blade with the X-Z crystal axes, and, e.g., rotating the blade about the X axis (by an angle θ) and rotating the crystal about the Z axis (by an angle φ). Alternatively, such cuts can be formed by aligning the saw blade (or the crystal) with the X-Z crystal axes, and then rotating the blade about the X axis and then the Z axis, or about the Z axis and then the X axis.

SC-cut crystals can have values for θ of about 35°, preferably about 35° 15', plus or minus about 20', and values for p of about 22°, preferably about 22° 0', plus or minus about 20'.

SC-cut crystal exhibits frequency-temperature behavior which is similar to that of the AT-cut, with the added feature that it shows essentially no change of frequency when the crystal is stressed. A monitor crystal fabricated from SC-cut material, in initial coating trials, exhibits none of the frequency changes induced by high-stress dielectrics on AT-cut crystals. Historically, SC-cut quartz has been a more expensive version of quartz, but the benefits for the optical process engineer may outweigh the cost penalty.

IT-cut crystals can have values for θ of about 34°–35°, preferably about 34° 24', plus or minus about 20', and values for φ of about 19°, preferably about 19° 6', plus or minus about 20'.

When IT-cut crystals are used in a quartz crystal thickness monitor as described herein, the IT-cut crystal surprisingly exhibits a lack of substantial response to radiation induced frequency changes caused by heat sources or hot deposition sources present in a high vacuum thin film deposition system. In addition, it has been found that an IT-cut quartz crystal exhibits very low stress induced frequency shifts. In addition, it has surprisingly been found that by heating an IT-cut quartz crystal in accordance with the present invention, the coating behaves better and the sensor performs even more accurately. In addition, for low stress performance, special circuitry is not required (whereas in the case of SC-cut quartz, it has been found that special circuitry is generally required).

The piezoelectric element can generally be of any suitable shape. Preferably, the piezoelectric element is substantially plano-convex or has opposite surfaces which are substantially flat and parallel. A preferred shape is generally cylindrical with the axial dimension being much smaller than the radial dimension. Preferably, the edges of the piezoelectric element are beveled, as is well known in the art.

The piezoelectric element is preferably mounted in a body. Such a body can be of any desired shape; preferably, the body supports the piezoelectric element along its perimeter, leaving a large inner portion of the piezoelectric element free to vibrate.

The first and second electrodes can be any structure capable of conducting electricity. As noted above, the first electrode is in contact with at least a first region of the piezoelectric element, and the second electrode is in contact with at least a second region of said piezoelectric element, the second region being spaced from the first region, whereby current from the power supply can pass through the first electrode, through the piezoelectric element from the first region to the second region, and through the second electrode.

Preferably, the first and second regions of the piezoelectric element are coated with electrode material. Preferably, the first and second regions of the piezoelectric element are coated with aluminum or aluminum alloy electrode material. For silicon dioxide coatings, such electrode regions can extend the useful life of the sensor by 100% or more when compared to the industry standard gold crystal electrode coatings. Furthermore, frequency shifts due to electrode adhesion failure are reduced up to 90 percent under standard laboratory conditions. The benefit this electrode brings tends to be material and deposition specific, as it is not the same for all coatings. Alternatively, any other suitable material, e.g., gold, can be used to form electrode coatings on the first and second regions.

Where a heater is employed, in general, any heater or heaters can be employed which are effective to heat the piezoelectric element to the desired temperature, and to maintain the piezoelectric element at such desired temperature. For example, any conduction heater, radiant healer or convection heater can be employed. Examples of suitable heaters include Kapton contact heaters (which are well known to those of skill in the art, i.e., which comprise a block with resistive wires positioned inside the block), quartz lamp infrared-heating sources, etc. Such heater or heaters can be positioned inside the body or clamped to the body (with the heat being conducted by the body into the piezoelectric element), or can be separate from the body but directed toward the piezoelectric element, or in any other suitable arrangement.

Preferably, the deposition is carried out in a vacuum. In such cases, the heater(s) should be conduction or radiant.

The temperature of the body may be monitored, e.g., using a thermocouple or a thermistor, in order to maintain the body (and the piezoelectric element) at a substantially constant temperature.

The frequency of vibration of the piezoelectric element is sensed using any suitable device. For example, skilled artisans are familiar with microprocessors which can be readily set up to read frequency of vibration of the piezoelectric element.

Similarly, any suitable device can be used to convert frequency of vibration data to deposition rate (e.g., Angstroms per second) and/or to accumulated coating values (i.e., total thickness, e.g., in Angstroms). For example, skilled artisans are familiar with setting up microprocessors to perform such conversions. A variety of algorithms for performing such calculations are well known to those of skill in the art (see, e.g., Chih-shun Lu, "Mass determination with piezoelectric quartz crystal resonators," *J. Vac. Sci. Technol.*, Vol. 12, No. 1, (January/February 1975), the entirety of which is hereby incorporated by reference). Corrections can be made to the thickness calculation algorithm to account for acoustic impedance, as is well known in the art.

In addition, well known electronics and shielding are preferably employed in order to eliminate radio frequency interference and voltage variations.

Figure 2:
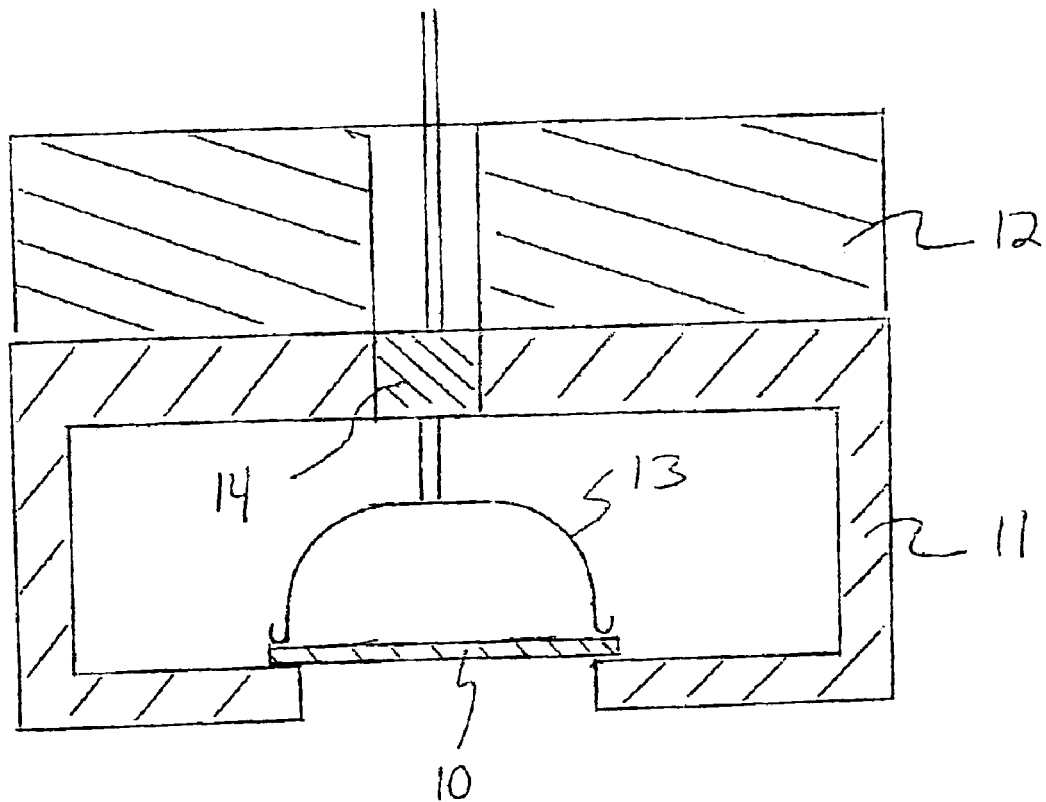
FIG. 2 is a schematic illustration of one example of an embodiment according to the present invention.

FIG. 2 schematically depicts one example of an embodiment according to the present invention. In the embodiment shown in FIG. 2, a generally cylindrical quartz crystal 10 is mounted on a body 11 made of a block of stainless steel with a center portion thereof milled out. A heated block 12 is in contact with the body 11 so as to heat the body 11 and the quartz crystal 10. The body 11, in contact with a bottom surface of the quartz crystal 10, acts as the first electrode, and a spring contact electrode 13, positioned between a collet 14 and a top surface of the quartz crystal, acts as the second electrode. Voltage is applied between the first electrode and the second electrode by a power supply (not shown). The spring contact electrode 13 minimizes extraneous vibrations.

As noted above, the method of measuring the thickness of a film and/or the rate of increase of the thickness of a film according to the present invention comprises applying a voltage across a piezoelectric element from a first electrode to a second electrode, thereby causing the piezoelectric element to vibrate, and measuring a rate of the vibration of the piezoelectric element. In one aspect of the present invention, heat may be applied to the piezoelectric element.

In the aspect of the invention where heat is applied to the piezoelectric element, preferably, the piezoelectric element is heated to (and maintained at) a temperature of at least about 50 degrees C., preferably at least about 100 degrees C., e.g., a temperature in a range of from about 100 degrees C. to about 120 degrees C., e.g., about 100 degrees C.

The present invention can be applied to the process monitoring and control of optical and "high stress" electrical thin film coatings used in the production of optical and electronic devices. This invention specifically applies to the production of thin films via high vacuum deposition processes.

A heated crystal sensor system utilizing the standard "AT-cut" quartz crystal will allow for more precise and longer lasting process control in high vacuum thin film deposition systems.

By heating the crystal up, to temperatures including 100 degrees C. (although benefits are observed over a range of 50 degrees C. and up), it is observed that the erratic performance of the crystal is minimized or even eliminated. An additional advantage of this improvement is that water lines, conventionally used to cool the crystal in the vacuum chamber can be eliminated. This simplifies installation in the vacuum system and eliminates the possibility of water leaks, a common problem.

Additionally, the IT-cut crystal does not respond to radiant heat transients or to stress build-up in thin dielectric films. This is critical in many optical coating processes since (1) bright light often accompanies the heating up of materials used to make the coating and (2) dielectric films make up the bulk of the materials used in optical coatings. Quartz has a definite "frequency-temperature" and "stress-frequency" behavior. As it heats up or is deformed, its vibrational frequency changes. This conflicts with the mechanism utilized in thin film thickness sensors, which register film thickness by linearly decreasing in vibrational frequency as a coating builds on the crystal surface. The IT-cut crystal eliminates this frequency shift brought on by radiant energy or stress. As a result, a heated IT-cut crystal is ideal for accurate measurement of thin optical films.

EXAMPLES

Samples of an "IT-cut" quartz crystal were used to monitor the coating of an optical material (magnesium fluoride) in a vacuum-processing chamber. This crystal type was chosen for an experiment to determine if the thermal properties of quartz could be changed to provide a more stable means of monitoring optical material depositions (as used in the lens making industry, for example). The standard crystal type in current use is referred to as "AT-cut" quartz and is very temperature and coating stress dependent. In the execution of this experiment, an infrared-heating source, a quartz lamp, was used to heat the crystal radiantly, in order to simulate the conditions present in typical industrial applications. This crystal did not register any noticeable frequency changes when the lamp was turned on, in marked contrast to the "AT-cut". This is a remarkable property, since it dramatically improves the accuracy of the sensor.

The above experiment was repeated, with the addition of a separate Kapton contact heater used to raise the operating temperature of the crystal as well. This heated crystal, while possessing the same lack of noticeable response to radiant heat effects as before, also operated longer and with much greater stability when used to monitor the magnesium fluoride optical film coating process. This experiment was repeated with an "AT-cut" crystal, also heated. A similar effect was observed. This is a marked improvement over the performance of the industry standard "AT-cut" that is normally water cooled (e.g., to about 20 degrees C.).

Any two or more structural parts of the devices described above can be integrated. Any structural part of the devices described above can be provided in two or more parts (which are held together, if necessary).

What is claimed is:

1. A device for measuring the thickness of a film and/or the rate of increase of the thickness of a film, comprising:
   at least one piezoelectric element, said piezoelectric element comprising IT-cut quartz crystal;
   a first electrode, said first electrode being in contact with at least a first region of said piezoelectric element;
   a second electrode, said second electrode being in contact with at least a second region of said piezoelectric element, said second region being spaced from said first region; and
   means for measuring a frequency of resonant vibration which is affected by accumulation of mass on a surface of said crystal.

2. A device as recited in claim 1, further comprising a power supply which applies a voltage between said first electrode and said second electrode across said piezoelectric element.

3. A device as recited in claim 1, further comprising a heater which heats said piezoelectric element.

4. A device as recited in claim 3, wherein said heater heats said piezoelectric element to a temperature of at least about 50 degrees C.

5. A device as recited in claim 3, wherein said heater is in contact with a body, said piezoelectric element being in contact with said body.

6. A method of measuring the thickness of a film and/or the rate of increase of the thickness of a film, comprising:
   applying a voltage across a piezoelectric element from a first electrode to a second electrode, thereby causing said piezoelectric element to undergo vibration, said first electrode being in contact with a first region of said piezoelectric element, said second electrode being in contact with a second region of said piezoelectric element, said piezoelectric comprising IT-cut quartz crystal; and
   measuring a rate of said vibration of said piezoelectric element affected by an increase of thickness of a film on said piezoelectric element.

7. A method as recited in claim 6, further comprising applying heat to said piezoelectric element.

8. A method as recited in claim 7, wherein said piezoelectric lement is maintained at a substantially constant temperature.

9. A method as recited in claim 7, wherein said piezoelectric element is maintained at a temperature of at least about 50 degrees C.

10. A method as recited in claim 7, wherein said applying heat to said piezoelectric element is carried out by contact heating a body, said piezoelectric element being heated thereby through direct or indirect contact with said body.

11. A method of depositing a film and measuring the thickness of the film and/or the rate of increase of the thickness of the film, comprising:
    depositing a material onto at least one substrate and at least one piezoelectric element, said piezoelectric element comprising IT-cut quartz crystal;
    applying a voltage across said piezoelectric element from a first electrode to a second electrode, thereby causing said piezoelectric element to undergo vibration, said first electrode being in contact with a first region of said piezoelectric element, said second electrode being in contact with a second region of said piezoelectric element; and
    measuring a rate of said vibration of said piezoelectric element affected by an increase of thickness of a film on said piezoelectric element.

12. A method as recited in claim 11, further comprising applying heat to said piezoelectric element.

13. A method as recited in claim 12, wherein said piezoelectric element is maintained at a substantially constant temperature.

14. A method as recited in claim 12, wherein said piezoelectric element is maintained at a temperature of at least about 50 degrees C.

15. A method as recited in claim 12, wherein said applying heat to said piezoelectric element is carried out by contact heating a body, said piezoelectric element being heated thereby through direct or indirect contact with said body.

* * * * *